United States Patent [19]

Lyons et al.

[11] Patent Number: 5,480,986
[45] Date of Patent: Jan. 2, 1996

[54] METAL COMPLEXES OF SUBSTITUTED GABLE PORPHYRINS AS OXIDATION CATALYSTS

[75] Inventors: James E. Lyons, Wallingford; Paul E. Ellis, Jr., Downingtown; Richard W. Wagner, Murrysville, all of Pa.

[73] Assignee: Sun Company, Inc. (R&M), Philadelphia, Pa.

[21] Appl. No.: 100,516

[22] Filed: Jul. 30, 1993

[51] Int. Cl.$^6$ ............ C07C 29/50; C07D 487/22
[52] U.S. Cl. ............................. 540/145; 568/910
[58] Field of Search ................... 540/145; 568/910

[56] References Cited

U.S. PATENT DOCUMENTS

| | | | |
|---|---|---|---|
| 4,895,680 | 1/1990 | Ellis et al. | 568/910 |
| 4,895,682 | 1/1990 | Ellis et al. | 568/910.5 |
| 4,900,871 | 2/1990 | Ellis et al. | 568/910.5 |
| 4,970,348 | 11/1990 | Ellis et al. | 568/399 |
| 5,118,886 | 6/1992 | Ellis et al. | 568/910 |
| 5,120,882 | 6/1992 | Ellis et al. | 568/910 |
| 5,280,115 | 1/1994 | Ellis, Jr. et al. | 540/145 |

OTHER PUBLICATIONS

Meier et al; *J. Chem. Soc.*, Chem. Comm., 923 (1989).
Tabushi et al., J. Amer. Chem. Soc. 105, 2901, (1983).
Tabushi et al., *Tet. Lett.*, 23, 1913 (1982).

*Primary Examiner*—Mukund J. Shah
*Assistant Examiner*—Pavanaram K. Sripada
*Attorney, Agent, or Firm*—Q. Todd Dickinson; Stephen T. Falk

[57] ABSTRACT

Transition metal complexes of Gable porphyrins having two porphyrin rings connected through a linking group, and having on the porphyrin rings electron-withdrawing groups, such as halogen, nitro or cyano. These complexes are useful as catalysts for the oxidation of organic compounds, e.g. alkanes.

21 Claims, No Drawings

METAL COMPLEXES OF SUBSTITUTED GABLE PORPHYRINS AS OXIDATION CATALYSTS

The Government of the United States of America has rights in this invention pursuant to Cooperative Agreement No. DE-FC21-90MC26029 awarded by the U.S. Department of Energy.

BACKGROUND OF THE INVENTION

Prior work by the present inventors has established that highly halogenated metalloporphyrins are superior catalysts for the rapid and selective oxidation of hydrocarbons; (U.S. Pat. Nos. 4,970,348; 4,900,871; 4,895,682; and 4,895,680). The presence of fluoro, chloro and bromo substituents on the porphyrin ring is believed to cause enhancement of oxidative stability and increased catalytic activity. The mechanism of oxidation of hydrocarbon substrate, S, is believed to occur as follows, but the invention is not restricted to this mechanism:

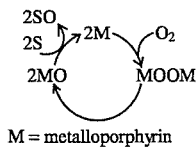

M = metalloporphyrin

Since it is necessary for two metalloporphyrin molecules to reductively bind the dioxygen molecule, the placement of both metal centers in the same molecule, as in a Gable porphyrin, would permit dioxygen binding between the metals, thereby enhancing the oxidation rate. The present invention concerns such a porphyrin and a process for using it to oxidize alkanes.

An ortho-Gable-porphyrin has been synthesized, see Meier, Kobuke and Kugimiya, *J. Chem. Soc., Chem. Commun.*, 1989, 923, wherein the biszinc complex, with two mesotriphenylporphins joined at the fourth meso position of each ring to ortho positions of a phenylene radical, is prepared in 70% yield after chromatographic separation.

SUMMARY OF THE INVENTION

According to the present invention, metal complexes of Gable porphyrins are prepared containing one or more electron-withdrawing substituents in the ligand portion of the molecule. A general formula for such compounds is:

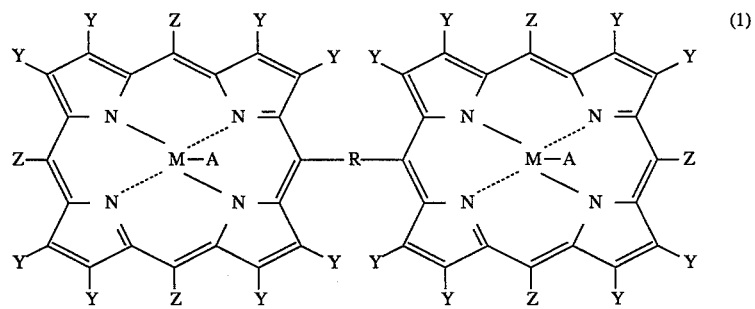

where M is a transition metal from Groups I, VI, VII or VIII of the Periodic Table, Y is hydrogen or alkyl, such as methyl, ethyl or homologs, or an electron-withdrawing substituent for hydrogen, Z is hydrocarbyl, halohydrocarbyl or halocarbyl, R is an aromatic group, and A is an anion or is absent. Preferred electron-withdrawing substituents are substituents such as chlorine, bromine, fluorine, nitro groups and cyano groups. Halogenation procedures such as those disclosed in U.S. Pat. No. 4,900,871 issued Feb. 13, 1990, in application U.S. Ser. No. 07/568,116 on halogenated metal porphyrins and metal phthalocyanines useful as oxidation catalysts and in application U.S. Ser. No. 07/634,261 on improved process for preparing perhaloporphyrin complexes, nitration procedures such as disclosed in U.S. Pat. No. 5,120,882 issued Jun. 9, 1992 and in application U.S. Ser. No. 07/892,106 filed Jun. 2, 1992, and cyanation procedures such as those disclosed in U.S. Pat. No. 5,118,886 issued Jun. 2, 1992 and application Ser. No. 07/892,107 filed Jun. 2, 1992, the disclosures of which are hereby incorporated by reference, may be used to introduce such electron-withdrawing substituents into the Gable porphyrins according to the invention.

The transition metal complexes of the Gable porphyrins of the invention are catalysts for the oxidation of organic compounds, for example alkanes, with those oxidizing agents for which transition metal complexes of porphyrins have known catalytic action. The preferred oxidizing agent for use according to the invention is molecular oxygen.

DETAILED DESCRIPTION OF THE INVENTION

In one embodiment of the invention, a Gable porphyrin is made according to the technique used in production of compounds (3), (4) and (5) of Meier et al., supra, but using pentafluorobenzaldehyde as the reagent in place of the benzaldehyde used to obtain compound (3) of Meier et al. The product obtained by the procedure according to this invention is a Gable porphyrin containing two molecules of mesotri(pentafluorophenyl)porphyrin joined at meso positions to ortho positions of a benzene ring. Metal, M, is inserted into the Gable porphyrin, and the product has the structure in compound (1) supra, where M is metal, for example iron, R is orthophenylene, each Z is pentafluorophenyl, and each Y is hydrogen. The metal, M, may be the same in each of the two porphyrin rings, for example iron, or different, for example iron and manganese.

Gable porphyrins according to the invention in which two porphyrin rings are attached at meta positions (see compound (1) of Meier et al supra), rather than ortho, positions of an aromatic ring, may be obtained by use of reagents whose selection is within the ability of persons skilled in the art in the light of the present specification.

Molecular modelling experiments show that fluorinated Gable porphyrins, in particular, have a hydrophobic pocket which attracts hydrocarbons and rejects oxygenates. These properties together with the increased reduction potentials due to electron-withdrawing groups give enhanced rates of hydrocarbon oxidation.

Other groups, for example naphthylene biphenylene, anthracene, or other aromatic groups, can be used in place of a phenylene group to create hydrophobic pockets of varying dimensions and provide shape selectivity useful in a variety of stereoselective and regioselective oxidative transformations.

Instead of pentahalobenzaldehydes, other halogenated aldehydes, for example trihaloacetaldehydes, perhalopropionaldehydes, perfluorobutyraldehydes and the like, having preferably 1 to 6 carbon atoms in the molecule, can be used to prepare Gable porphyrins having the structure of compound (1), supra, where M is metal, R is phenylene, each Z is perfluoroalkyl, for example trifluoromethyl, and each Y is hydrogen. Post functionalization of the pyrrole hydrogens to produce in one embodiment a Gable porphyrin as in compound (1) supra, with electron withdrawing groups such as halogen, nitro or cyano in Y positions of that compound further enhances the activity of these catalysts for the oxidation of alkanes by oxygen containing gas. In such post functionalized Gable porphyrins, each Y is, independently of the others, hydrogen, halogen, nitro or cyano. Where each Y is halogen, each porphyrin ring is perhalogenated.

Thus, a family of catalysts in which electron-deficient Gable porphyrin structures serve as activating binucleating macrocycles for oxidation active metal centers such as iron, manganese, chromium, ruthenium, cobalt and the like are provided according to the invention.

In one embodiment of the invention, the compositions according to the invention are bismetal (II)-Gable-porphyrins having electron-withdrawing substituents on beta positions of the porphyrin rings. In another embodiment, the compositions according to the invention are bismetal (III) derivatives with axial anionic ligands such as halide, azide, hydroxide, and others as in our patents supra. In still another embodiment, the compositions according to the invention are bismetal (II) derivatives which have the external axial sites blocked by strongly-coordinating neutral ligands such as pyridyl, attached to the metal through the nitrogen atom of the pyridine ring. Such ligands are too large to enter the hydrophobic cavity, thereby enhancing oxygen binding and hydrocarbon activation in the hydrophobic pocket rather than at the external axial positions in the Gable-porphyrin catalyst.

The chemoselectivity of the oxidation catalyzed by the compounds of the invention depends on the oxidant used, the metal center and the choice of reaction conditions, the selection of which is within the ability of the person skilled in the art in the light of the present specification. Regioselectivity and stereoselectivity are determined by the shape and size of the hydrophobic pocket in the porphyrin binucleating macrocycle.

Metals which can be used in the compounds according to the invention are those which are known for use in complexing porphyrins to provide active oxidation catalysts. Transition metals from Groups I, VI, VII and VIII of the Periodic Table, for example copper (Group I), chromium (Group VI), manganese (Group 7), and iron and ruthenium (Group VIII) are preferred, iron being particularly preferred.

Substrates other than alkanes can be oxidized according to the invention, for example alkyl aromatics, olefinic hydrocarbons, aldehydes, and others.

The following Examples illustrate the invention.

EXAMPLE 1

Dithianyl-protected o-phthalaldehyde, obtained from o-phthalaldehyde and propane-1,2-dithiol, is cyclized with pentafluorobenzaldehyde and pyrrole by the procedure of Meier et al., J. Chem. Soc., Chem. Commun., 1989, referring to Lindsey et al, J. Org. Chem. 1987, 52,827, to produce o-dithianyl-tri(pentafluorophenyl)porphyrin via the corresponding porphyrinogen.

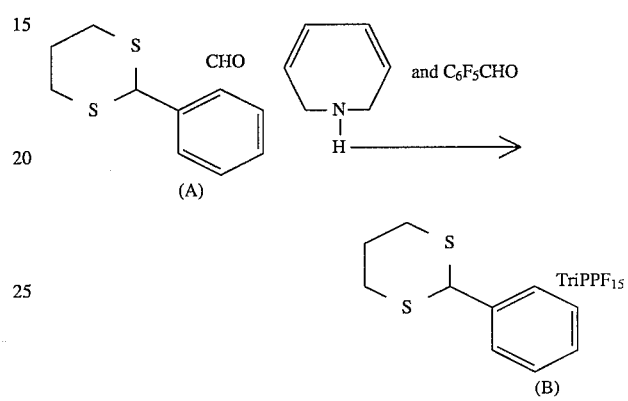

TRIPPF$_{15}$ = meso-tri(pentaflourophenyl)porphyrin

A 2 l flask fitted with reflux condenser is charged with 1.5 l of $CH_2Cl_2$, pentafluorobenzaldehyde (1.39 g, 11.25 mmol) pyrrole (1.04 g, 15 mmol) and (A) (0.84 g, 3.75 mmol). After stirring for a few minutes, 1.98 ml of 2.5M $BF_3OEt_2$ is added by syringe. This is stirred under $N_2$ for 1 hour. At this time, 2,3-dichloro-5,6-dicyano-1,4-benzoquinone (DDQ) (2.55 g, 11.25 mmol) is added. The reactor contents are refluxed for 1 hour and then cooled and evaporated to dryness. Compound B is purified by chromatography on alumina.

The dithianyl group in compound B is then subjected to oxidative/hydrolytic cleavage by reaction with $SO_2Cl_2$, by similar method to that used by Meier et al supra to produce their compound (4). The product of such cleavage in this example is o-formyltri(pentafluorophenyl)-porphyrin, Compound C below. In this step, Compound B is treated with sulfuryl chloride, dropwise, in $CH_2Cl_2$ at 0° with wet silica gel. After purification, the aldehyde group has replaced the thioacetyl group.

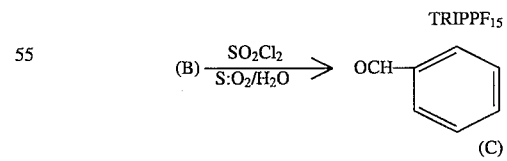

Compound C is subjected to a second Lindsey-type tri(pentafluorophenyl)porphyrin-ring construction with pentafluorobenzaldehyde and pyrrole, to give the Gable porphyrin, orthodi [mesotri(pentafluorophenyl)porphin]-benzene. In this step, Compound C is reacted again with pyrrole and pentafluorobenzaldehyde in a 1,4,3 molar ratio with $BF_3OEt_2$ catalyst to give the desired

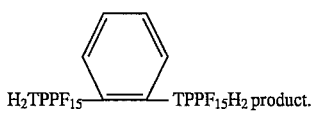

The bisiron complex, Fe$_2$, of the Gable porphyrin is made by reaction of the Gable porphyrin with an iron salt, e.g. FeCl$_2$·4H$_2$O, in a solvent, e.g. refluxing dimethylformamide or tetrahydrofuran, typically under reflux conditions, and chromatographically separated as

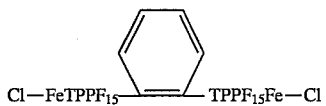

EXAMPLE 2

The bisiron complex of the Gable porphyrin obtained according to Example 3 is reacted with nitrogen dioxide to give the bisiron complex of orthodi[mesotri(pentafluorophenYl) β-tetranitroporphin] benzene, (Cl-FeTPPF$_{15}$(NO$_2$)$_4$C$_6$H$_4$TPPF$_{15}$(NO$_2$)$_4$F-Cl), with the predominant product having at least one nitro group on each of the two porphyrin rings. 0.5 g of the bisiron complex starting material is dissolved in 300 ml of methylene dichloride. Nitrogen-dioxide gas is bubbled through the solution for 5 minutes. The reaction mixture is then stirred at room temperature. The CH$_2$Cl$_2$ is removed by evaporation and the NO$_2$ complex purified by column chromatography or recrystallization in hot tetrahydrofuran.

EXAMPLE 3

Insertion of Zn into H$_2$TPPF$_{15}$(o-phenylene)TPPF$_{15}$H$_2$
1.0 g of H$_2$TPPF$_5$(o-phenylene)TPPF$_{15}$H$_2$ is dissolved in 150 ml of DMF. At reflux under N$_2$ 1.5 g of Zn(OAC)$_2$ is added with stirring. After 15 minutes, the reaction is cooled, filtered and 200 ml of H$_2$O is added which causes precipitation of the product ZnTPPF$_{15}$(o-phenylene)TPPF$_{15}$Zn which is washed with H$_2$O and dried.

EXAMPLE 4

Chlorination of ZnTPPF$_5$(o-phenylene)TPPF$_{15}$Zn 0.5 g of the gable porphyrin, ZnTPPF$_{15}$(o-phenylene)TPPF$_{15}$Zn is dissolved in 250 ml of CCl$_4$. At reflux Cl$_2$ gas is bubbled slowly through the solution for 5 minutes. Reflux is continued for 1 hour then HCl gas is bubbled through the solution for 1 minute to remove the Zn while the solution is still hot. The solution is cooled, washed with 100 ml of 5% NaHCO$_3$ then dried and chromatographed on neutral aluminum yielding H$_2$TPPF$_{15}$β-Cl$_8$(o-phenylene)TPPF$_{15}$β-Cl$_8$H$_2$.

EXAMPLE 5

Iron Insertion Method:
250 mg of H$_2$TPPF$_{15}$β-Cl$_8$(o-phenylene)TPPF$_{15}$β-Cl$_8$H$_2$ is dissolved in 75 ml of DMF with 5 ml of glacial acetic acid. The contents are degassed with N$_2$ before heating to 140°. 100 mg of FeCl$_2$·4H$_2$O is added in powder form. After stirring for 15–30 minutes at reflux, the contents are cooled, filtered and added to 100 ml of saturated aqueous NaCl solution cooled to about 5°. A brown flocculate occurs after overnight which is filtered and worked up with H$_2$O then dried in vacuo. Purification is achieved by chromatography on neutral alumina giving Cl-FeTPPF$_{15}$β-Cl$_8$(o-phenylene)-TPPF$_{15}$β-Cl$_8$Fe-Cl.

To obtain a Gable porphyrin wherein one ring is complexed with iron and the other with manganese for example, iron may be inserted into the porphyrin ring in an o-formyl intermediate to the Gable porphyrin, compound C in Example 1, and manganese into the second porphyrin ring in the Gable porphyrin product formed in the second ring construction as described in Example 1.

When trifluoroacetaldehyde for example is used in the reaction with pyrrole in the process according to the invention, the product is the bisiron complex of the Gable porphyrin, orthodi[mesotri-(trifluoromethyl)porphin]R where R is aromatic, e.g. benzene.

What is claimed is:
1. A composition of matter comprising Gable porphyrins having the formula:

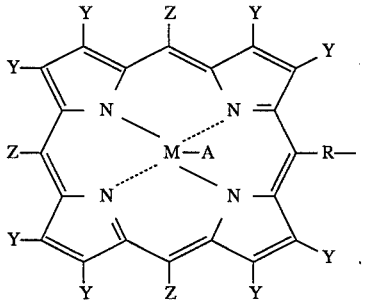

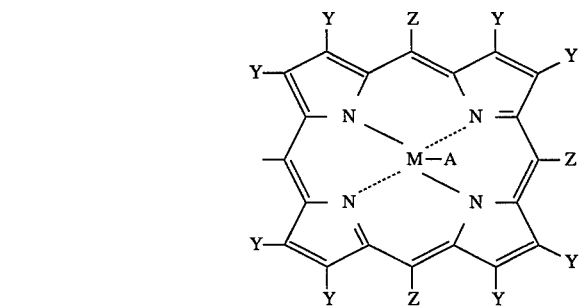

wherein M is a transition metal from selected from Groups I, VI, VII or VIII of the Periodic Table; Y is hydrogen or alkyl or an electron-withdrawing substituent for hydrogen; Z is halohydrocarbyl or halocarbyl; R is an aromatic group; and A is an anion or is absent.

2. The composition according to claim 1 wherein M is iron.
3. The composition according to claim 1 wherein at least one Y is halogen.
4. The composition according to claim 3 wherein each Y is halogen.
5. The composition according to claim 3 wherein at least one Y is bromine.
6. The composition according to claim 4 wherein each Y is bromine.
7. The composition according to claim 1 wherein each Z is halophenyl.
8. The composition according to claim 7 wherein each Z is pentafluorophenyl.
9. The composition according to claim 1 wherein each Z is haloalkyl.
10. The composition according to claim 9 wherein each Z is perfluoroalkyl.
11. The composition according to claim 10 wherein each Z is trifluoromethyl.

12. The composition according to claim 1 wherein at least one Y is nitro.

13. The composition according to claim 12 wherein at least one Y in each ring is nitro.

14. The composition according to claim 1 wherein at least one Y is cyano.

15. The composition according to claim 14 wherein at least one Y in each ring is cyano.

16. The composition according to claim 1 wherein each Z is pentafluorophenyl and each Y is halogen.

17. The composition according to claim 1 wherein each Z is trifluoromethyl and each Y is halogen.

18. The composition according to claim 1 wherein each Y is ethyl.

19. The composition according to claim 1 wherein R is ortho-phenylene.

20. The composition according to claim 1 wherein R is meta-phenylene.

21. The compositions according to claim 1 wherein R is selected from the group consisting of phenylene, biphenylene, naphthylene and anthracene.

* * * * *

UNITED STATES PATENT AND TRADEMARK OFFICE
CERTIFICATE OF CORRECTION

PATENT NO. : 5,480,986
DATED : January 2, 1996
INVENTOR(S) : James E. Lyons
Paul E. Ellis
Richard W. Wagner It is certified that error appears in the above-indentified patent and that said Letters Patent is hereby corrected as shown below:

Column 5, line 22: delete "(pentafluorophenYl) and insert -- (pentafluorophenyl)--

Column 5, line 23: delete "(Cl-FeTPPF$_{15}$(NO$_2$)$_4$F-Cl)" and insert --(Cl-FeTPPF$_{15}$(NO$_2$)$_4$Fe-Cl)--

Column 5, line 37: delete "H$_2$TPPF$_5$" and insert -- H$_2$TPPF$_{15}$ --

Column 5, line 46: delete "ZnTPPF$_5$" and insert -- ZnTPPF$_{15}$ --

Signed and Sealed this

Eleventh Day of November, 1997

Attest:

BRUCE LEHMAN

Attesting Officer

Commissioner of Patents and Trademarks